(12) United States Patent
Huston et al.

(10) Patent No.: US 12,109,405 B2
(45) Date of Patent: Oct. 8, 2024

(54) METHODS AND APPARATUSES FOR REDUCING BLEEDING VIA ELECTRICAL TRIGEMINAL NERVE STIMULATION

(71) Applicant: The Feinstein Institutes for Medical Research, Manhasset, NY (US)

(72) Inventors: Jared M. Huston, New York, NY (US); Jason R. Fritz, New York, NY (US); Seema G. Amin, New York, NY (US); Christopher J. Czura, Lake Grove, NY (US); Kevin J. Tracey, Old Greenwich, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 0 days.

(21) Appl. No.: 18/303,991

(22) Filed: Apr. 20, 2023

(65) Prior Publication Data
US 2023/0270996 A1    Aug. 31, 2023

Related U.S. Application Data

(62) Division of application No. 16/391,155, filed on Apr. 22, 2019, now Pat. No. 11,660,443.

(60) Provisional application No. 62/660,915, filed on Apr. 20, 2018.

(51) Int. Cl.
| | |
|---|---|
| *A61N 1/04* | (2006.01) |
| *A61H 23/00* | (2006.01) |
| *A61N 1/36* | (2006.01) |
| *A61N 7/00* | (2006.01) |

(52) U.S. Cl.
CPC ............ *A61N 1/0468* (2013.01); *A61H 23/00* (2013.01); *A61N 1/36034* (2017.08); *A61N 7/00* (2013.01); *A61H 2201/10* (2013.01); *A61N 2007/0017* (2013.01)

(58) Field of Classification Search
None
See application file for complete search history.

(56) References Cited

U.S. PATENT DOCUMENTS

| | | | |
|---|---|---|---|
| 2,164,121 | A | 6/1939 | Pescador |
| 3,363,623 | A | 1/1968 | Atwell |
| 3,709,228 | A | 1/1973 | Barker |
| 4,073,296 | A | 2/1978 | McCall |
| 4,098,277 | A | 7/1978 | Mendell |
| 4,632,095 | A | 12/1986 | Libin |
| 4,702,254 | A | 10/1987 | Zabara |

(Continued)

FOREIGN PATENT DOCUMENTS

| | | |
|---|---|---|
| DE | 20316509 U1 | 4/2004 |
| GB | 04133 A | 2/1910 |

(Continued)

OTHER PUBLICATIONS

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

(Continued)

*Primary Examiner* — Michael W Kahelin
(74) *Attorney, Agent, or Firm* — Shay Glenn LLP

(57) ABSTRACT

Disclosed are apparatuses and methods for reducing or limiting bleeding (e.g., blood loss and/or bleeding time) in an animal by trigeminal stimulation. The apparatuses and methods may activate one or more branches of the trigeminal nerve. This activation may be invasive or non-invasive.

14 Claims, 4 Drawing Sheets

(56) References Cited

U.S. PATENT DOCUMENTS

| | | |
|---|---|---|
| 5,073,560 A | 12/1991 | Wu et al. |
| 5,106,853 A | 4/1992 | Showell et al. |
| 5,154,172 A | 10/1992 | Terry, Jr. et al. |
| 5,175,166 A | 12/1992 | Dunbar et al. |
| 5,231,988 A | 8/1993 | Wernicke et al. |
| 5,330,507 A | 7/1994 | Schwartz |
| 5,330,515 A | 7/1994 | Rutecki et al. |
| 5,403,845 A | 4/1995 | Dunbar et al. |
| 5,472,841 A | 12/1995 | Jayasena et al. |
| 5,496,938 A | 3/1996 | Gold et al. |
| 5,503,978 A | 4/1996 | Schneider et al. |
| 5,514,168 A | 5/1996 | Friedman |
| 5,567,588 A | 10/1996 | Gold et al. |
| 5,571,150 A | 11/1996 | Wernicke et al. |
| 5,580,737 A | 12/1996 | Polisky et al. |
| 5,582,981 A | 12/1996 | Toole et al. |
| 5,618,818 A | 4/1997 | Ojo et al. |
| 5,637,459 A | 6/1997 | Burke et al. |
| 5,654,151 A | 8/1997 | Allen et al. |
| 5,683,867 A | 11/1997 | Biesecker et al. |
| 5,705,337 A | 1/1998 | Gold et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,853,005 A | 12/1998 | Scanlon |
| 5,854,289 A | 12/1998 | Bianchi et al. |
| 5,902,814 A | 5/1999 | Gordon et al. |
| 5,977,144 A | 11/1999 | Meyer et al. |
| 6,006,134 A | 12/1999 | Hill et al. |
| 6,028,186 A | 2/2000 | Tasset et al. |
| 6,083,696 A | 7/2000 | Biesecker et al. |
| 6,110,900 A | 8/2000 | Gold et al. |
| 6,110,914 A | 8/2000 | Phillips et al. |
| 6,124,449 A | 9/2000 | Gold et al. |
| 6,127,119 A | 10/2000 | Stephens et al. |
| 6,140,490 A | 10/2000 | Biesecker et al. |
| 6,147,204 A | 11/2000 | Gold et al. |
| 6,168,778 B1 | 1/2001 | Janjic et al. |
| 6,171,795 B1 | 1/2001 | Korman et al. |
| 6,208,902 B1 | 3/2001 | Boveja |
| 6,210,321 B1 | 4/2001 | Di Mino et al. |
| 6,407,095 B1 | 6/2002 | Lochead et al. |
| 6,473,644 B1 | 10/2002 | Terry, Jr. et al. |
| 6,528,529 B1 | 3/2003 | Brann et al. |
| 6,602,891 B2 | 8/2003 | Messer et al. |
| 6,610,713 B2 | 8/2003 | Tracey |
| 6,721,603 B2 | 4/2004 | Zabara et al. |
| 6,735,471 B2 | 5/2004 | Hill et al. |
| 6,838,471 B2 | 1/2005 | Tracey |
| 7,117,033 B2 | 10/2006 | Shalev et al. |
| 7,204,815 B2 | 4/2007 | Connor |
| 7,373,204 B2 | 5/2008 | Gelfand et al. |
| 8,010,189 B2 | 8/2011 | Shalev |
| 8,380,315 B2 | 2/2013 | DeGiorgio et al. |
| 8,506,469 B2 | 8/2013 | Dietrich et al. |
| 8,606,371 B2 | 12/2013 | Garfield et al. |
| 8,688,220 B2 | 4/2014 | DeGiorgio et al. |
| 8,696,724 B2 | 4/2014 | Rogers |
| 8,729,129 B2 | 5/2014 | Tracey et al. |
| 8,914,114 B2 | 12/2014 | Tracey et al. |
| 8,958,880 B2 | 2/2015 | DeGiorgio et al. |
| 9,101,766 B2 | 8/2015 | Nekhendzy |
| 9,579,507 B2 | 2/2017 | Cakmak |
| 9,656,069 B1 | 5/2017 | Danilov et al. |
| 9,656,078 B1 | 5/2017 | Danilov et al. |
| 9,789,306 B2 | 10/2017 | Sabourin et al. |
| 11,260,229 B2 | 3/2022 | Manogue |
| 11,660,443 B2 | 5/2023 | Huston et al. |
| 2002/0040035 A1 | 4/2002 | Myers et al. |
| 2002/0086871 A1 | 7/2002 | O'Neill et al. |
| 2002/0099418 A1 | 7/2002 | Naritoku et al. |
| 2002/0116030 A1 | 8/2002 | Rezai |
| 2003/0176818 A1 | 9/2003 | Schuler et al. |
| 2004/0048795 A1 | 3/2004 | Ivanova et al. |
| 2004/0193231 A1 | 9/2004 | David et al. |
| 2004/0204355 A1 | 10/2004 | Tracey et al. |
| 2004/0240691 A1 | 12/2004 | Grafenberg |
| 2004/0249416 A1 | 12/2004 | Yun et al. |
| 2005/0021092 A1 | 1/2005 | Yun et al. |
| 2005/0075701 A1 | 4/2005 | Shafer |
| 2005/0075702 A1 | 4/2005 | Shafer |
| 2005/0137218 A1 | 6/2005 | Tracey et al. |
| 2005/0149145 A1 | 7/2005 | Coulter |
| 2005/0165459 A1 | 7/2005 | Coulter |
| 2005/0197675 A1 | 9/2005 | David et al. |
| 2006/0064139 A1 | 3/2006 | Chung et al. |
| 2006/0100668 A1 | 5/2006 | Ben-David et al. |
| 2006/0122675 A1 | 6/2006 | Libbus et al. |
| 2006/0178703 A1 | 8/2006 | Huston et al. |
| 2006/0206155 A1 | 9/2006 | Ben-David et al. |
| 2006/0229677 A1 | 10/2006 | Moffitt et al. |
| 2006/0287678 A1 | 12/2006 | Shafer |
| 2007/0100263 A1 | 5/2007 | Merfeld |
| 2008/0045882 A1 | 2/2008 | Finsterwald |
| 2008/0281197 A1 | 11/2008 | Wiley et al. |
| 2010/0004709 A1 | 1/2010 | Mische |
| 2011/0178441 A1 | 7/2011 | Tyler |
| 2012/0071795 A1 | 3/2012 | Khokhlova et al. |
| 2012/0203301 A1 | 8/2012 | Cameron et al. |
| 2013/0150756 A1 | 6/2013 | Vitek et al. |
| 2014/0106430 A1 | 4/2014 | Hargrave et al. |
| 2014/0107542 A1 | 4/2014 | Schubert et al. |
| 2014/0148832 A1 | 5/2014 | Walton et al. |
| 2014/0343599 A1 | 11/2014 | Smith et al. |
| 2015/0359511 A1 | 12/2015 | Uchiumi et al. |
| 2016/0158534 A1 | 6/2016 | Guarraia et al. |
| 2016/0250097 A9 | 9/2016 | Tracey et al. |
| 2016/0310315 A1 | 10/2016 | Smith |
| 2017/0007820 A9 | 1/2017 | Simon et al. |
| 2017/0197081 A1 | 7/2017 | Charlesworth et al. |
| 2017/0361094 A1 | 12/2017 | Cartledge et al. |
| 2017/0368329 A1 | 12/2017 | Tyler et al. |
| 2018/0021217 A1 | 1/2018 | Tracey et al. |
| 2018/0207450 A1 | 7/2018 | Sanchez et al. |
| 2019/0030334 A1 | 1/2019 | Lerman et al. |
| 2020/0046992 A1 | 2/2020 | Tracey et al. |
| 2020/0406065 A1 | 12/2020 | Puleo et al. |
| 2021/0251848 A1 | 8/2021 | Tracey et al. |
| 2023/0019961 A1 | 1/2023 | Huston et al. |
| 2023/0117074 A1 | 4/2023 | Zanos et al. |

FOREIGN PATENT DOCUMENTS

| | | |
|---|---|---|
| WO | WO97/30998 A1 | 8/1997 |
| WO | WO01/08617 A1 | 2/2001 |
| WO | WO02/44176 A1 | 6/2002 |
| WO | WO02/057275 A1 | 7/2002 |
| WO | WO03/072135 A2 | 9/2003 |
| WO | WO2005/092308 A2 | 10/2005 |
| WO | WO2008/112915 A1 | 9/2008 |
| WO | WO2018/081826 A1 | 5/2018 |
| WO | WO2020/006048 A1 | 1/2020 |

OTHER PUBLICATIONS

Ellington et al., In vitro selection of RNA molecules that bind specific ligands, Nature, vol. 346, pp. 818-822, Aug. 30, 1990.

Holladay et al., Neuronal nicotinic acetylcholine receptors as targets for drug discovery, Journal of Medicinal Chemistry, 40(26), pp. 4169-4194, Dec. 1997.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Jaeger et al., The structure of HIV-1 reverse transcriptase complexed with an RNA pseudoknot inhibitor, The EMBO Journal, 17(15), pp. 4535-4542, Aug. 1998.

(56) References Cited

OTHER PUBLICATIONS

Joshi et al., Potent inhibition of human immunodeficiency virus type 1 replection by template analog reverse transcriptase, J. Virol., 76(13), pp. 6545-6557, Jul. 2002.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Lenovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Schneider et al., High-affinity ssDNA inhibitors of the review transcriptase of type 1 human immunodeficiency virus, Biochemistry, 34(29), pp. 9599-9610, Jul. 1995.

Snyder et al., Correction of hemophilia B in canine and murine models using recombinant adeno-associated viral vectors; Nature Medicine, 5(1), pp. 64-70, Jan. 1999.

Tracey, K.J., The inflammatory reflex, Nature, vol. 420, pp. 853-859, Dec. 19-26, 2002.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Wikipedia; Trigeminal Nerve; retrieved from the internet (http://en.wikipedia.org/wiki/Trigeminal_nerve) on Sep. 6, 2022; 12 pages.

12.5-17.5 V, 30 Hz, 2 ms, 10 min

METHODS AND APPARATUSES FOR REDUCING BLEEDING VIA ELECTRICAL TRIGEMINAL NERVE STIMULATION

CROSS REFERENCE TO RELATED APPLICATIONS

This patent application is a divisional of U.S. patent application Ser. No. 16/391,155, titled "METHODS AND APPARATUSES FOR REDUCING BLEEDING VIA ELECTRICAL TRIGEMINAL NERVE STIMULATION," filed on Apr. 22, 2019, now U.S. Patent Application Publication No. 2019/0321623, which claims priority to U.S. Provisional Patent Application No. 62/660,915, titled "METHODS AND APPARATUSES FOR REDUCING BLEEDING VIA ELECTRICAL TRIGEMINAL NERVE STIMULATION," filed on Apr. 20, 2018, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is generally related to preventing and/or treating bleeding in a subject. More specifically, this disclosure is related to apparatuses (devices, systems, and methods) for preventing and/or treating bleeding in a patient through stimulation of the trigeminal nerve.

BACKGROUND

Blood loss may lead to a variety of problems, including dysregulation or ultimately death. Blood loss can occur due to a various causes. For example, there are approximately 100,000,000 surgeries performed annually in the United States, with millions more worldwide (CDC, National Center for Health Statistics) and these generally have an inherent risk of bleeding, from minor to potentially life threatening. Aside from administration of tranexamic acid for select orthopedic procedures, there are no prophylactic systemic therapies available to administer to help improve hemostasis and minimize surgical bleeding.

Trauma is the third leading cause of death in the United States (CDC, National Center for Health Statistics). A common cause of death following traumatic injury is uncontrolled bleeding (CDC, National Center for Health Statistics). While modern tourniquets are sometimes available to help staunch hemorrhage following extremity trauma, these injuries are still dangerous. Approaches to control non-compressible torso hemorrhage remain even more limited and this is a common cause of death of U.S. soldiers on the battlefield.

Postpartum hemorrhage (PPH) is the leading cause of maternal deaths worldwide. The most common cause is poor contraction of the uterus. Other causes include uterine tears, retained placenta, and inadequate blood clotting. In the United States, approximately 11% of maternal deaths result from PPH, whereas in the developing world approximately 60% of maternal deaths result from PPH. This equates to 100,000 to 140,000 deaths per year. Existing treatments include medications such as oxytocin, misoprostol, and ergotamine, intravenous fluids, blood transfusions, and uterine massage. Surgery to repair cervical or vaginal lacerations or uterine rupture is sometimes necessary as well. Many of these therapeutic options are risky or unavailable in resource-poor areas, resulting in dramatically higher mortality rates.

Hemophilia A is an X-linked recessive disorder associated with spontaneous and prolonged bleeding episodes secondary to deficiencies in clotting factor VIII. More than 20,000 individuals in the United States suffer from this life-long disease. Up to 30% of children with severe hemophilia cannot receive standard factor VIII concentrates due to the development of inhibitor antibodies. Maintaining hemostasis then requires bypassing agents, such as activated prothrombin complex concentrate and recombinant factor VIIa, to help generate clot via alternative pathways. These costly therapies are associated with serious systemic thrombotic side effects, including myocardial ischemia, deep venous thrombosis, and pulmonary embolism. Thus there is a need for new devices, methods, and systems to prevent and treat bleeding problems.

Described herein are devices, methods, and systems that may address the issues identified above.

SUMMARY OF THE DISCLOSURE

The present invention relates to controlling bleeding in a patient. More specifically, this disclosure is related to apparatuses (devices, systems) and methods for controlling bleeding and bleeding time in a patient through neural stimulation, such as through electrical and/or mechanical stimulation of the trigeminal nerve. The apparatus may provide invasive or non-invasive stimulation. Controlling bleeding may include preventing and/or treating bleeding (e.g., surgical bleeding, traumatic bleeding, bleeding related to other medical procedures or conditions, and inherited or acquired bleeding disorders).

For example, described herein are methods of reducing bleeding (e.g., one or more of bleed time or blood volume loss) in a subject, the method comprising: applying one or more of mechanical or electrical stimulation to the subject's trigeminal nerve; and reducing bleeding by at least 20%.

Also described herein are methods of treating a bleeding subject that include determining when the subject is bleeding and applying one or more of mechanical or electrical stimulation to the subject's trigeminal nerve to reduce bleeding by stimulating the trigeminal nerve (e.g., at between 0.1 Hz and 100 Hz for greater than 10 minutes).

Also described herein are methods of method of reducing bleeding time in a subject undergoing a surgery that include: applying one or more of mechanical or electrical stimulation to the subject's trigeminal nerve during the surgery or within 2 hours of performing the surgery on the subject; wherein the mechanical or electrical stimulation comprises stimulating the trigeminal nerve (e.g., at between 0.1 Hz and 100 Hz for greater than 10 minutes). The method may further include reducing bleeding by greater than 10% (e.g., greater than 20%, greater than 30%, greater than 40%, etc.).

Also described herein are methods of reducing or limiting blood loss in a hemorrhaging subject that include: applying one or more of mechanical or electrical stimulation to the subject's trigeminal nerve at between 0.1 Hz and 100 Hz for greater than 10 minutes; and reducing blood loss from the hemorrhage by at least 10%.

Also described herein are methods of treating a hemophiliac subject that include: determining when the subject is bleeding; and applying one or more of mechanical or electrical stimulation to the subject's trigeminal nerve to reduce bleeding. The method may also include reducing bleeding by greater than 10%. Applying one or more of mechanical or electrical stimulation may include stimulating the trigeminal nerve at between 0.1 Hz and 100 Hz for greater than 10 minutes.

Also described herein are methods of reducing bleeding in a subject that has been treated with an anticoagulant that include: applying one or more of mechanical or electrical stimulation to the subject's trigeminal nerve at between 0.1 Hz and 100 Hz for greater than 10 minutes; and reducing bleeding by at least 20%.

In any of these methods, applying one or more of mechanical or electrical stimulation may comprise stimulating the trigeminal nerve at between 0.1 Hz and 100 Hz for greater than 10 minutes. Applying one or more of mechanical or electrical stimulation may comprises applying electrical stimulation noninvasively to the subject's trigeminal nerve. For example, in any of these methods, applying one or more of mechanical or electrical stimulation may comprise applying electrical stimulation between 1-50 Hz and between 0.5-15 V having a pulse width of between 0.5 ms and 10 ms.

Applying one or more of mechanical or electrical stimulation may comprise applying non-invasive mechanical stimulation.

In any of these methods, applying one or more of mechanical or electrical stimulation may comprise applying one or more of mechanical or electrical stimulation to one of an ophthalmic, maxillary or mandibular branch of the subject's trigeminal nerve. Alternatively, applying one or more of mechanical or electrical stimulation may comprise applying one or more of mechanical or electrical stimulation to two or more of an ophthalmic, maxillary or mandibular branch of the subject's trigeminal nerve.

In general, applying may comprise applying one or more of mechanical or electrical stimulation to sensory fibers of the patient's trigeminal nerve. Applying may comprise applying unilateral stimulation to the subject's trigeminal nerve or applying bilateral stimulation to the subject's trigeminal nerve.

Reducing bleeding may include reducing bleeding time and/or reducing lost blood volume. For example, reducing bleeding may include reducing bleeding time by at least 10% (e.g., at least 20%, at least 30%, at least 40%, etc.) as compared to an untreated subject. Reducing bleeding may include reducing bleeding volume by at least 10%, at least 20%, at least 30%, at least 40%, etc. as compared to an untreated subject.

In general, any of the methods described herein may reduce bleeding by applying one or more of mechanical or electrical stimulation without triggering a diver's reflex in the subject. Alternatively or additionally, any of these methods may reduce bleeding by applying one or more of mechanical or electrical stimulation without stimulating the vagus nerve.

Thus, in any of these methods, applying may comprise non-invasively applying one or more of mechanical or electrical activation. Alternatively, in any of these methods applying may comprise applying from an implant (e.g., implanted neuromodulator that is in communication with the trigeminal nerve).

In any of these methods, the subject may be human or non-human.

Applying may include applying one or more of mechanical or electrical activation to one or more of an ophthalmic, maxillary and/or mandibular branch of the subject's trigeminal nerve. For example, applying may comprise applying one or more of mechanical or electrical activation to sensory fibers of the patient's trigeminal nerve. In some variation, applying may be limited to applying via the sensory fibers. In some variations, applying comprises applying unilateral activation to the subject's trigeminal nerve. Alternatively, applying may comprise applying bilateral activation to the subject's trigeminal nerve.

As mentioned, any of these methods may include reducing bleeding time. For example, reducing bleeding time may comprises reducing bleeding time from of one or more of an internal hemorrhage or an external hemorrhage. Bleeding time may be reduced (e.g., the application of electrical and/or mechanical energy may be applied until the bleeding time is reduced) by more than 10%, 15%, 20%, 25%, 30%, 35%, 40%, 45%, 50%, etc. compared to untreated patients. Blood loss may be reduced (e.g., the application of electrical and/or mechanical energy may be applied until the blood loss is reduced) by more than 10%, 15%, 20%, 25%, 30%, 35%, 40%, 45%, 50%, etc.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 8, between 12.5 V and 17.5 V at 3 Hz and 2 ms pulses were applied for 10 min to an external site over the trigeminal nerve, resulting in a significant reduction on bleeding time.

DETAILED DESCRIPTION

Figure 1:
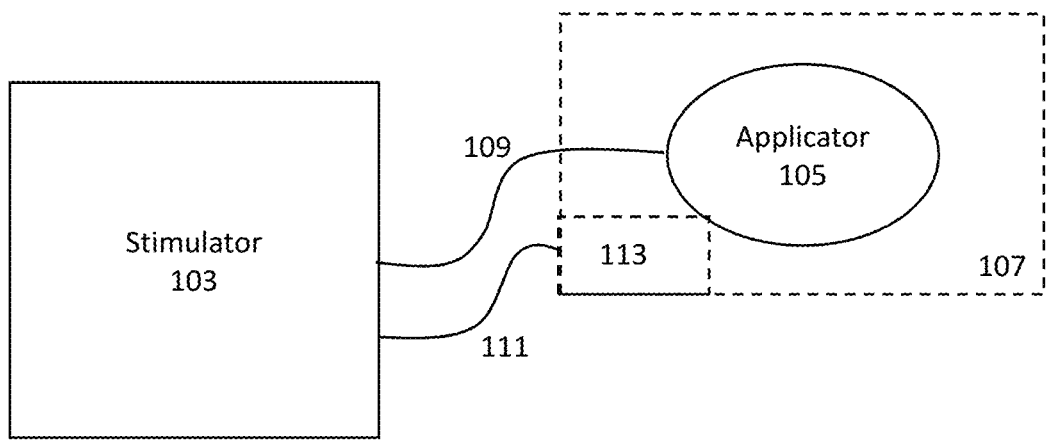
FIG. 1 is a schematic illustration of a trigeminal nerve stimulation apparatus that may be used to reduce bleeding, including by reducing bleeding time and/or blood loss as described herein.

The present invention relates to controlling, e.g., treating and/or preventing, bleeding in a patient by stimulation of the patient's trigeminal nerve. More specifically, described herein are apparatuses (devices, systems, and methods) for controlling bleeding by applying trigeminal nerve stimulation to achieve one or more of: reducing bleeding time, reducing bleeding volume (blood loss) and/or both. The trigeminal nerve may be stimulated electrically and/or mechanically. Controlling bleeding may include preventing and/or treating bleeding such as surgical bleeding, traumatic bleeding, bleeding related to childbirth, bleeding related to other medical procedures or conditions, bleeding mediated or increased by anticoagulants, inherited or acquired bleeding disorders such as hemophilia, and so forth.

As used herein, "treatment" includes prophylactic and therapeutic treatment. "Prophylactic treatment" refers to treatment before the onset of a condition (e.g., bleeding, an inflammatory condition, etc.) is present, to prevent, inhibit or reduce its occurrence.

As used herein, a patient or subject may be any animal, preferably a mammal, including a human, but can also be a companion animal (e.g., a cat or dog), a farm animal (e.g., a cow, a goat, a horse, a sheep) or a laboratory animal (e.g., a guinea pig, a mouse, a rat), or any other animal.

"Bleeding time" or "bleed time" as used herein refers to the length of time it takes to for bleeding to stop. In general, bleeding time may be controlled or influenced by how well blood platelets work to form a platelet plug. In an untreated subject, bleeding time is generally increased by the administration of anticoagulant, such as aspirin, heparin, and warfarin.

As used herein, the terms "reduce" or "reducing" when referring to bleeding, e.g., bleeding time and/or blood loss, encompass at least a small but measurable reduction in bleeding over non-treated controls. Reduction may be at least 5%, at least 10%, at least 20%, at least 30%, at least 40%, at least 50%, at least 60%, or more than 60% or anything within these ranges. For example, a value between these ranges may be chosen so as to use a protocol or apparatus configured to reduce bleeding while minimizing side effects due to applied trigeminal nerve stimulation.

The nervous system controls nearly every cell and organ in the body through signals carried by nerves. Such signals allow the nervous system to monitor for tissue injury and then to initiate a healing process. The methods and apparatuses described herein are generally configured for modulating signals on the trigeminal nerve, for example by targeted electrical nerve stimulation, to effectively treat or prevent bleeding. Trigeminal nerve stimulation (TNS) as described herein is a method to reduce bleeding following tissue injury or other bleeding event. Trigeminal nerve stimulation as described herein may be non-invasive or minimally invasive. In some examples, TNS may be a non-invasive or minimally invasive method to activate the trigeminal nerve. Electrical stimulation may be, for example, transcutaneous (without breaching the skin) or direct (e.g., through an implant and/or needle electrode). Non-invasive stimulation typically does not require a surgery, and does not expose the trigeminal nerve fiber(s) or require direct contact with the trigeminal nerve fiber(s). As used herein, non-invasive stimulation can be achieved, for example, by mechanical (e.g., pressure, vibration, etc.) and/or electrical (e.g. electromagnetic radiation) means applied externally to the subject.

Although in some examples, a non-invasive or minimally invasive approach as described herein may be used in conjunction with a pharmacological approach (e.g., for an additive or a synergistic benefit), in general an approach described herein may be more efficacious, safer, and less costly than traditional pharmacological therapies. Advantages of this method over pharmacological approaches may include higher specificity, fewer side effects, lower costs, and improved compliance. Advantages over implantable pulse generators for chronic nerve stimulation applications may include avoidance of surgery and associated complications, both for the initial procedure and subsequent procedures for battery changes, and lower costs.

The trigeminal nerve (cranial nerve V) is the largest of the cranial nerves, and has three different branches or nerve distributions (V1, V2, V3, also referred to as the ophthalmic nerve, maxillary nerve and mandibular nerve, respectively) that converge on the trigeminal ganglion. The trigeminal nerve is paired and present on both sides of the body. The trigeminal nerve relays sensory and motor information between the brain and the face and tongue. Trigeminal nerve stimulation (TNS) is thought to activate multiple structures in the brain and brainstem, such as the locus coeruleus (LC) and nucleus tractus solitarius (NTS). TNS is clinically approved in Europe for the treatment of medically refractory epilepsy and depression.

The method and apparatuses described herein may be configured to treat bleeding by applying stimulation, e.g., mechanical and/or electrical stimulation, to one or more regions of the trigeminal nerve, and/or a nucleus or ganglion associated with the trigeminal nerve such as the trigeminal nucleus, the principal nucleus, semilunar ganglion or gasserian ganglion, and the mesencephalic nucleus. The stimulation may be primarily afferent, primarily effect, or both afferent and efferent. For example, the stimulation may be applied to one or more branches of the trigeminal nerve (the ophthalmic nerve, the maxillary nerve and/or the mandibular nerve).

Invasive stimulation may be applied by one or more tissue-penetrating electrodes, such as needle electrodes, paddle electrodes, cuff electrodes, or the like. The electrodes may be in contact with a portion of the trigeminal nerve or they may be proximate to the trigeminal nerve. Trigeminal stimulation may be applied by implanted device, such as one or more implanted electrodes that are place on or near a portion of the trigeminal nerve and/or a nucleus or ganglion associated with the trigeminal nerve. The implant may be for extended use (e.g., over many days, weeks, months or years). Alternatively, the methods and apparatuses described herein may be acutely inserted into the tissue at or near a portion of the trigeminal nerve. For example a method or apparatus may include an applicator (e.g., electrode, mechanical transducer, etc.) that is inserted into the patient to apply energy acutely to one or more regions of the trigeminal nerve. For example one or more needle electrodes may be inserted into the patient's skin to apply trigeminal stimulation.

In some variations non-invasive stimulation may be applied to the trigeminal nerve. The non-invasive stimulation may be electrical or mechanical. For example, electrical stimulation may be applied through the skin or mouth (transdermally) from one or more locations. Alternatively or additionally, non-invasive stimulation may be applied mechanically through the skin, for example, by applying a mechanical applicator such as a mechanical transducer, to the skin (or within the mouth) over or near a portion of the trigeminal nerve. A mechanical transducer may apply oscillating mechanical force and/or pressure to the trigeminal nerve. In some variations the mechanical transducer may be an ultrasound transducer that applies acoustic energy (one form of mechanical energy) to the trigeminal nerve. When non-invasive stimulation is applied to the mouth it may be to the tongue and/or region of the cheeks, sublingually, etc.

Stimulation of the trigeminal nerve may be applied to any of the cutaneous dermatomes) of the three branches of the trigeminal nerve. The trigeminal nerve may be stimulated by applying stimulation to the ophthalmic nerve from the scalp and forehead region, the upper eyelid, the conjunctiva and cornea of the eye, the nose (including the tip of the nose, except alae nasi), and/or the nasal mucosa. Alternatively or additionally, the trigeminal nerve may be stimulated by applying stimulation to the maxillary nerve from the lower eyelid and cheek, the nares and upper lip, the upper teeth and gums, the nasal mucosa, the palate and/or the roof of the pharynx. Alternatively or additionally, the trigeminal nerve may be stimulated by applying stimulation to the mandibular nerve from the lower lip, the lower teeth and gums, the chin and jaw, the external ear and/or the tongue.

In some embodiments, activating the trigeminal nerve (e.g., by electrical, mechanical and/or other stimulation) might not include (and need not include) activating the vagus nerve. For example, the vagus nerve might be activated indirectly due to trigeminal nerve activation or might not be activated. Any of the methods for controlling bleeding by activating the trigeminal nerve described herein may include indirectly activating the vagus nerve. In some variations, activating the trigeminal nerve includes activating neuronal structures without direct stimulation of the vagus nerve. In some examples, activating the trigeminal nerve includes activating the cholinergic anti-inflammatory pathway and/or any other steps to control bleeding or bleeding time in a subject as described in U.S. Pat. No. 8,729,129, without direct stimulation of the vagus nerve. Although activating the trigeminal nerve may include not activating the vagal nerve, in some variations, the vagus nerve might be activated, either directly or indirectly. In some particular examples, activating the vagus nerve-mediated reduced bleed-time safely and efficaciously is through electrical stimulation of the trigeminal nerve, utilizing precise and specific electrical stimulation parameters. Trigeminal nerve and vagal nerve stimulation may include improving hemostasis via accelerated clot formation such as at the site of tissue injury. This may lead to less blood loss and a shorter duration of bleeding following tissue trauma and hemorrhage.

The methods for controlling bleeding described herein may be performed by any appropriate apparatus, including a trigeminal nerve stimulation apparatus useful for stimulating the trigeminal nerve. Preliminary work has suggested that a modified version of a trigeminal nerve stimulation apparatus such as the Monarch™ eTNS device (Neurosigma™), which is CE mark-approved in the European Union, Canada, and Australia, may be used. This apparatus includes a patch for contacting part of the body (e.g., head) of a subject and delivering pulsed electrical stimulus through the patch. Such a device may be adapted for use to deliver non-invasive electrical stimulation to the V1 branch of the trigeminal nerve.

FIG. 1 is a schematic of a generic trigeminal stimulation apparatus to treat bleeding. In this example, the apparatus generally includes a trigeminal stimulator 103 that is connected to an applicator 105 for applying stimulation to the trigeminal nerve. A frame or securement 107 may optionally be used to secure the applicator in communication with the trigeminal nerve. For example, the applicator may be an electrode for applying trigeminal stimulation non-invasively, such as to the skin or within the mouth; surface electrodes may include skin electrodes, plate electrodes, or the like. The stimulator may be directly connected to the applicator via one or more wires 109. The frame or securement may be part of a worn or wearable structure (bandage, headband, hat, helmet, etc.). In some variations the stimulator may be integrated with the applicator and/or with a frame or securement. Any of the apparatuses described herein may include one or more inputs, including user (physician, caregiver, nurse, etc.) controls. Any of these apparatuses may also or alternatively include one or more sensors 113 for detecting a condition of the patient; sensor data may be used to control the apparatus and may feed into the stimulator via a wired or wireless connection 111. Sensors may detect one or more of: blood loss/bleeding, blood pressure, heart rate, etc.

In an implantable device, the stimulator may be external or internal and included with the applicator within the body. Alternatively, in some variations the stimulator may be at least partially external and may apply energy to the applicator either wired or wirelessly (e.g., by induction).

As mentioned, in some variations the applicator may be a mechanical applicator (including, but not limited to an acoustic applicator). The applicator may apply force to the trigeminal nerve (e.g., pressure) to stimulate the trigeminal nerve. The mechanical applicator may include a piezoelectric element, a motor, or any other appropriate actuator.

Although the stimulation described in the examples herein was primarily electrical stimulation applied at a predetermined range of intensities and frequencies applied by inserted electrodes, preliminary data suggests other types of invasive and non-invasive stimulation can be used (e.g. non-invasive mechanical stimulation, non-invasive electrical stimulation, etc.), including minimally invasive, subcutaneous stimulation. Non-invasive stimulation may be performed by one or more electrodes or actuators that do not contact the nerve.

In general, the stimulation described herein may be sufficient to result in coordinated stimulation of a bundle of trigeminal nerves, either afferent, efferent or both. The coordinate stimulation may include sub-threshold (e.g., below the threshold to result in an action potential) or supra-threshold (e.g., resulting in one or more action potentials) on the nerve(s). Coordinated stimulation may mean that some percentage of the fibers (nerve fibers) of all or a portion of the trigeminal nerve are stimulated together. This percentage may be specific to afferent fiber or efferent fibers, and/or may be specific to one or more of the nerves of the trigeminal. For example, coordinated stimulation may be simultaneous or essentially simultaneous stimulation of 0.01% or more, 0.1% or more, 1% or more, 2% or more 3% or more, 4% or more, 5% or more, 7% or more, 10% or more, 15% or more, 20% or more, etc., of the trigeminal nerve or a portion of the trigeminal nerve (e.g., the ophthalmic nerve, maxillary nerve and mandibular nerve, or branches of any of these).

When electrical energy is applied to stimulate the trigeminal nerve to control bleeding, the electrical energy may be applied within an effective voltage and/or current range. For example, the electrical stimulation may be in the range of 10 mV to 30 V (e.g., between about 1 V and 20 V, between about 2 V and 20 V, between about 3 V and 20 V, between about 3 V and 19 V, between about 3 V and 18 V, between about 3 V and 17 V, between about 3 V and 15 V, between about 3 V and 14 V, between about 3 V and 12 V, between about 3 V and 10 V, etc.). The current may be between about 1 mA and 100 mA (e.g., between about 1 mA and 70 mA, between about 1 mA and 60 mA, between about 1 mA and 50 mA, etc.). The stimulation may be a frequency of between about 0.1 Hz to 100 Hz (e.g., between about 0.1 Hz and 75 Hz, between about 1 Hz and 50 Hz, between about 0.1 Hz and 50 Hz, between about 1 Hz and 50 Hz, between about 0.1 Hz and 40 Hz, between about 1 Hz and 40 Hz, between about 0.1 Hz and 30 Hz, between about 1 Hz and 30 Hz, etc.). Non-invasive electrical stimulation may be applied using slightly higher parameter values in order to penetrate to the trigeminal nerve region(s).

In any of the types stimulation described herein, the stimulation may be applied for a duration of between about 1 ms to about 1 hour (e.g., about 1 min to 45 min, about 1 min to 30 min, about 1 min to 20 min, about 1 min to 10 min, etc.). In some variations the stimulation may be applied for longer than 1 hour. In some variations the stimulation may be applied until a reduction in bleeding is detected or the apparatus is manually shut off. There may be an off-time or delay between rounds of stimulation. For example, the off-time or delay may be greater than 10 min, greater than 20 min, greater than 30 min, greater than 45 min, greater than 1 hour, greater than 2 hours, greater than 3 hours, greater than 4 hours, greater than 5 hours, greater than 6 hours, greater than 12 hours, etc.

Mechanical stimulation may be oscillatory, repeated, pulsatile, or the like. In some variations the non-invasive stimulation may the repeated application of a mechanical force against the subject's skin at a predetermined frequency for a predetermined period of time. For example, the non-invasive mechanical stimulation may be a mechanical stimulation with a spectral range from 1 to 700 Hz (e.g., between about 1 to 500 Hz, between about 10 to 700 Hz, between about 20 to 500 Hz, between about 50 to 500 Hz, etc.) at an amplitude that ranges between 0.0001-5 mm displacement. The temporal characteristics of the mechanical stimulation may be specific to the location of the applicator. In some variations the frequency of stimulation is varying or non-constant. The frequency may be varied, e.g., between about 1 Hz and 500 Hz (e.g., −/+5%, 10%, 15%, 20%, 25%, 30%, 35%, 50%, etc.). In some variations the frequency is constant. In general the frequency refers to the frequency of the pulsatile stimulation within an "on period" of stimulation. Multiple stimulation periods may be separated by an "off period" extending for hours or even days, as mentioned above.

The force with which the mechanical stimulation is applied may also be constant, or it may be variable. Varying the force and/or frequency may be beneficial to ensure that the mechanical stimulation is effective during the entire period of stimulation, particularly if the effect of non-invasive stimulation operates at least in part through mechanoreceptors such as the rapidly acclimating Pacinian corpuscles. Similarly, applied electrical stimulation may be varied (e.g., by varying the frequency and/or amplitude, such as the current amplitude and/or voltage amplitude, e.g., within the effective range).

As mentioned above, when applying stimulation to the trigeminal nerve to control bleeding, the non-invasive stimulation may be scheduled or timed in a specific manner. For example, a period of stimulation ("on stimulation") may be followed by a period during which stimulation is not applied ("off period"). The off period may be much longer than the on period. For example, the off period may be greater than an hour, greater than two hours, greater than four hours, greater than 8 hours, greater than 12 hours, greater than 24 hours, or greater than 2 days. The on period is the duration of a stimulation (which may include a frequency component), and may be less than 10 minutes, less than 5 minutes, less than 2 minutes, less than 1 minute, etc. The ratio of the on period and the off period may partially determine the duty cycle of stimulation.

In some examples, either one (e.g., left or right) of the two paired trigeminal nerves may be activated (e.g., unilateral activation). In some examples, the paired trigeminal nerves may be both be activated in a subject (e.g., bilateral activation). In some examples, part or all of the trigeminal nerve may be activated. For example, any one, two or three of the three different branches or nerve distributions (V1, V2, and V3) may be activated. In some examples, sensory fibers of the trigeminal nerve are stimulated. Alternatively or additionally, a nucleus or ganglion of the trigeminal may also or instead be stimulated. Additionally or alternatively, associated nerves that are connected to the trigeminal nerve may be stimulated.

Stimulation may be performed using one or more patches configured to cover part of the body each containing one or more electrodes (an array of 2, 3, 4, 5, 10, or more electrodes) configured to cover part of the body (e.g. cheek, forehead, head, neck, nose, scalp, etc.) in a position sufficient to provide stimulation one or more parts of a trigeminal nerve. Stimulation may be performed using one or more electrodes configured to be placed under the skin, such as in a muscle and 1, 2, 3, 4, 5, 10, or more electrodes) may be placed in a muscle.

Also described herein are apparatuses (devices, systems, and methods) for activating the trigeminal nerve and the vagal nerve. In some embodiments, both the trigeminal nerve and the vagal nerve may be directly activated (e.g., by electrical, mechanical or other stimulation such as magnetic, thermal, etc.).

Although in some examples, the apparatuses and methods described herein may be used to activate the dive reflex (or dive response) under particular conditions, however, in general, they do not and need not activate the dive reflex. Further, in some variations, the trigeminal stimulation described herein may not activate the dive reflex. The dive reflex in general can activated, for example, by submerging the body in cold water (and holding the breath) wherein the body overrides basic homeostatic functions. The dive reflex is a physiological adaptation that regulates respiration, heart rate, and arterial blood pressure in a particular way. Although all mammals control breathing, heart rate, and arterial blood pressure during their lives, these controls are strongly altered during diving and activation of the dive reflex. In general, trigeminal stimulation parameters may be chosen so as to not activate the dive reflex (e.g., trigeminal stimulation without inducing a dive reflex). Failure to induce a dive reflex may be failure to invoke a percentage change in heart rate and/or respiration and/or arterial blood pressure by more than a predetermined amount. For example, failure to induce a dive reflex may be failure to reduce one or more of heart rate and/or respiration and/or arterial blood pressure by greater than about 2%, 5%, 7%, 10%, 15%, 20%, 25%, 30%, 40%, etc.

The apparatuses and methods described herein may be suitable for therapeutically or prophylactically treating subjects suffering from or at risk from suffering from unwanted bleeding from any cause such as: bleeding disorders including but not limited to afibrinogenemia, Factor II deficiency, Factor VII deficiency, fibrin stabilizing factor deficiency, Hageman Factor deficiency, hemophilia A, hemophilia B, hereditary platelet function disorders (e.g., Alport syndrome, Bernard-Soulier Syndrome, Glanzmann thrombasthenia, gray platelet syndrome, May-Hegglin anomaly, Scott syndrome, and Wiskott-Aldrich syndrome), parahemophilia, Stuart Power Factor deficiency, von Willebrand disease, thrombophilia, or acquired platelet disorders (such as those caused by common drugs: antibiotics, and anesthetics, blood thinners, and those caused by medical conditions such as: chronic kidney disease, heart bypass surgery, and leukemia), childbirth, injury, menstruation, and surgery. An unwanted bleeding treated using any of the apparatuses or methods described herein may include an internal hemorrhage or an external hemorrhage. An internal hemorrhage includes a hemorrhage in which blood is lost from the vascular system inside the body, such as into a body cavity or space. An external hemorrhage includes blood loss outside the body.

Preliminary data for trigeminal stimulation applied either before or during an injury resulting in bleeding has shown a significant reduction in bleeding as measured by either bleed time or total volume of blood loss of greater than 20%, e.g., greater than 30%, greater than 40%, etc. For example, in some of the experiments described herein bleeding was reduced by approximately 45% or more using non-invasive, mechanical stimulation of the trigeminal nerve.

EXAMPLES

Figure 2:
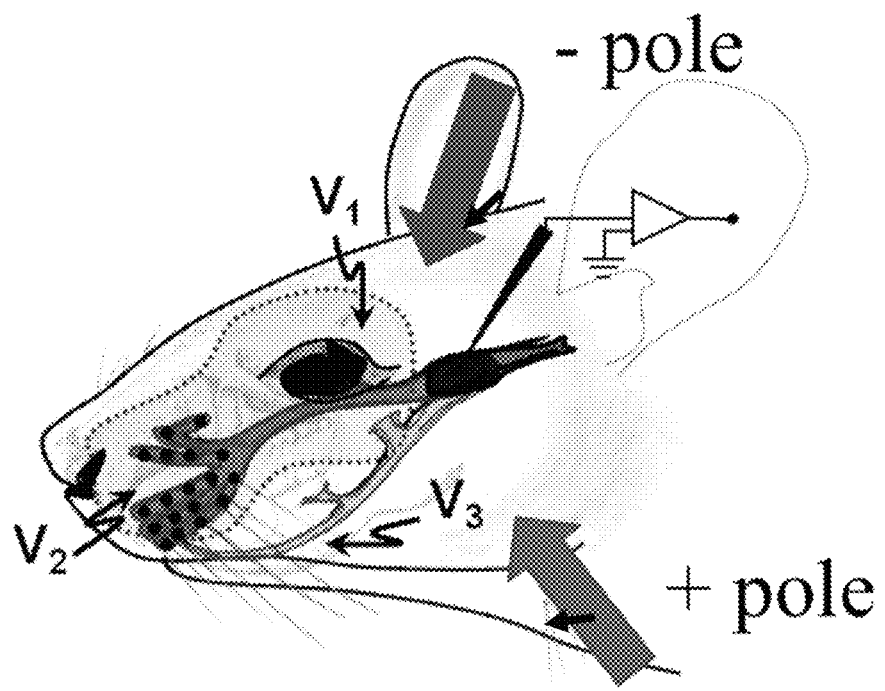
FIG. 2 shows one example of a technique for stimulating the trigeminal nerve of an animal (e.g., mouse) model to reduce bleeding as described herein.

FIG. 2 illustrates an experimental set-up that was used to illustrate the application of trigeminal stimulation to reduce bleeding. In this set-up, the stimulation device includes two single, monopolar, stainless steel needle electrodes (0.38 mm, Technomed, White Bear Lake, MN) attached to an MP36R Data Acquisition System (Biopac Systems, Goleta, CA) attached to a low voltage stimulation adaptor (Biopac Systems, Goleta, CA). The positive (+) pole electrode (see +pole arrow in FIG. 2) was inserted subcutaneously into the left masseter muscle. The negative (−) pole electrode (see −pole arrow in FIG. 2) was inserted subcutaneously in the midline of the skull, midway between the caudal border of the ipsilateral eye and cranial border of the ipsilateral ear. This spatial arrangement likely maximizes current flow across all three branches ($V_1$, $V_2$, $V_3$) of the trigeminal nerve as they course back to the brain (see the block wedge in FIG. 2).

The effect of trigeminal stimulation was robustly demonstrated in an animal model using an apparatus such as that schematically illustrated in FIG. 2. In this example, constant voltage stimuli (e.g., 2 V or 5 V, 30 Hz, 2 ms pulse width, monophasic) was applied for 10 minutes, 20 minutes, or 30 minutes duration. One complete operational cycle included a 2 V or 5 V monophasic, rectangular pulse stimulus lasting 2 milliseconds. This cycle was repeated at 30 Hz such as 10 minutes, 20 minutes, or 30 minutes.

Adult male 8-12 week old C57BL/6J mice (20-25 g, Taconic) and male 12-16 week old factor VIII knockout mice (20-25 g, Jackson Labs) were housed at 25° C. on a 12-hour light/dark cycle. Standard animal chow and water were freely available. All animal experiments were performed in accordance with the National Institutes of Health (NIH) Guidelines.

Animals were anesthetized with ketamine (144 mg/kg, i.p.) and xylazine (14 mg/kg, i.p.). After seven minutes, animals were placed in the right lateral decubitus position, and the positive pole needle electrode was inserted subcutaneously into the left masseter muscle. The negative pole needle electrode was inserted subcutaneously in the midline of the skull, midway between the ipsilateral eye and cranial border of the ipsilateral ear.

In a first set of experiments, a constant voltage stimuli (2 V or 5 V, 30 Hz, 2 ms pulse width) was applied for 10 minutes, 20 minutes, or 30 minutes. Electrical stimuli were generated using an MP36R Data Acquisition System (Biopac Systems, Inc., Goleta, CA) attached to an out 3 low voltage stimulation adapter. Sham-stimulated animals underwent insertion of the needle electrodes but no electricity was delivered.

Following trigeminal nerve stimulation (TNS) or sham stimulation, tails were immersed in water at 37±1° C. for five minutes. Tails were then removed from the solution, 2 mm of tail was amputated with a razor blade, and immediately placed into a 50 mL beaker containing water at 37° C. Tails were allowed to bleed uncontrolled until bleeding stopped for a minimum of ten seconds. This duration of bleeding was recorded as bleeding time. For analyses of bleeding in factor VIII mice, tails were first immersed in 0.9% saline at 37° C. for 5 min. Tails were then removed and 2 mm of tail amputated with a razor blade. Tails were then placed into a 10 mL conical tube containing 0.9% saline at 37° C. Tails were allowed to bleed uncontrolled for a total of ten minutes. Total blood loss was measured using densitometry and the samples were read at 550 nm. A standard curve was created from a known volume of blood.

Figure 3:
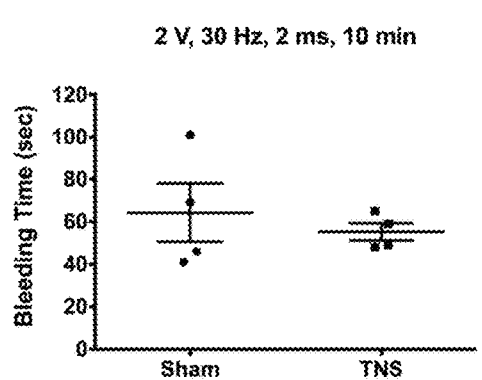
FIG. 3 is a graph showing bleeding times for mice after treatment with a low level of electrical energy applied to the trigeminal nerve.
Figure 4:
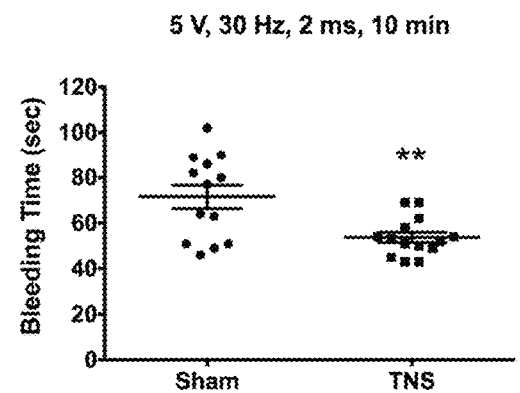
FIG. 4 is a graph showing a reduction in bleeding time for mice after the application of a 5 V electrical stimulation applied to the trigeminal nerve for 10 minutes.

As shown in FIGS. 3 and 4, electrical stimulation of the trigeminal nerve dose dependently reduced bleeding time in a murine model of arterial tail injury and hemorrhage. In FIG. 3, initial stimulation parameters (2 V, 30 Hz, 2 ms, 10 min) did not significantly reduce bleeding time (TNS=55.3±4.1 sec vs. Sham 64.3±13.7 sec, n=4/group, p=NS). This appears to be because the applied stimulation was below a threshold for activating the reduction in bleeding from activation of the trigeminal nerve. For example, similar stimulation at a higher voltage resulted in a significant reduction in bleeding. In FIG. 4, when stimulation intensity was increased (5 V, 30 Hz, 2 ms, 10 min), there was a significant reduction in bleeding time (TNS=53.7±2.2 sec vs. Sham=71.5±5.1 sec, n=13-14/group, p<0.01).

Figure 5:
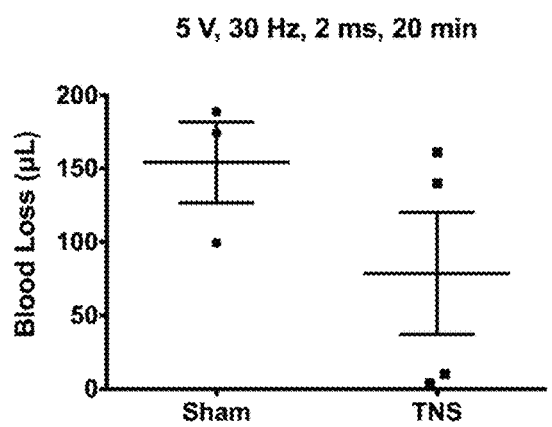
FIG. 5 is a graph showing a reduction in blood loss in mice after the application of a 5 V electrical stimulation applied to the trigeminal nerve for 20 minutes.
Figure 6:
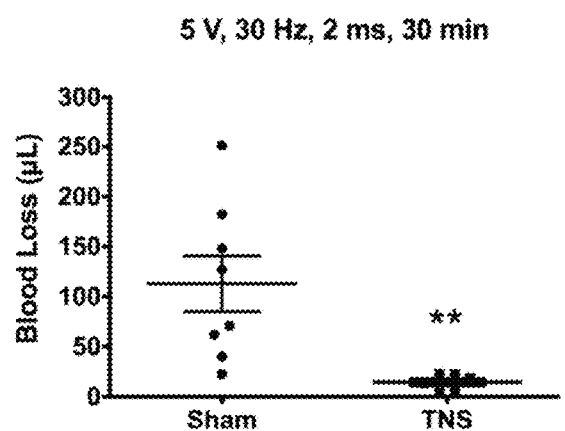
FIG. 6 is a graph showing a reduction in blood loss in mice after the application of a 5 V electrical stimulation to the trigeminal nerve for 30 minutes.

A significant effect was also seen in the reduction in blood loss when treating with trigeminal nerve stimulation. For example, FIGS. 5 and 6 show that the effect of electrical stimulation of the trigeminal nerve dose dependently reduced blood loss in a murine model of hemophilia A (F8 KO) and arterial tail hemorrhage. As shown in FIG. 5, although initial stimulation parameters (5 V, 30 Hz, 2 ms, 20 min) did not consistently reduce blood loss in the hemophilia A mice (TNS=78.7±41.5 μL vs. Sham 154.2±27.8 μL, n=3-4/group, p=NS), when stimulation duration was lengthened (shown in FIG. 6, applying 5 V, 30 Hz, 2 ms, 30 min), there was a significant reduction in blood loss (TNS=14.4±3.4 μL vs. Sham=113.0±27.8 μL, n=6-8/group, p=0.01).

Figure 7:
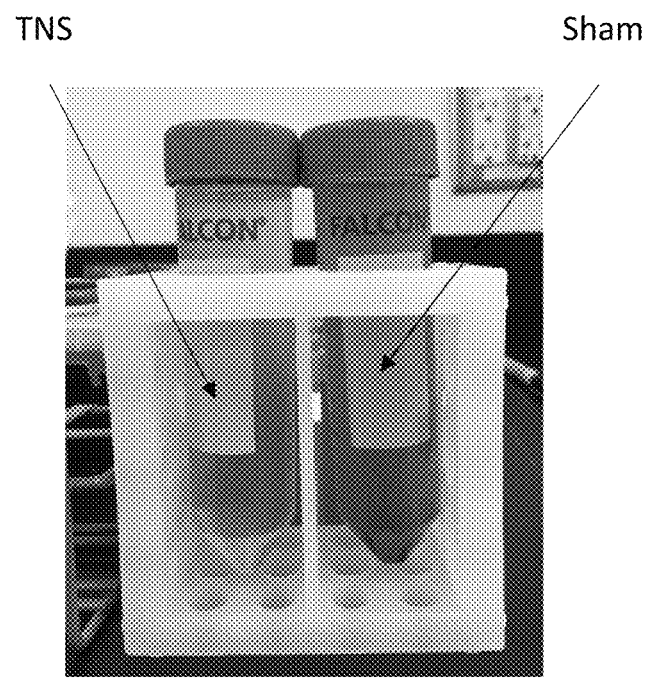
FIG. 7 shows two collection tubes holding blood obtained from a mouse pretreated with trigeminal nerve stimulation (left) and a mouse that to which sham stimulation was applied (right). Trigeminal nerve stimulation significantly reduced bleeding in mice after electrical current stimulation compared with a sham treated mice. The tube on the right from the sham treated mouse has significantly more blood than the tube on the left from the treated mouse.

FIG. 7 illustrates the total blood collected from an untreated (right, sham) animal as compared to a treated (left, TNS) animal. As shown graphically in FIG. 6, significantly more blood was collected from untreated animals as compared to animals in which trigeminal stimulation was applied.

In any of the methods and apparatuses described herein, TNS can modulate both the patient's sympathetic nervous system (SNS) and parasympathetic nervous system (PNS) activities to reduce bleeding time.

As mentioned above, any of these methods and apparatuses may be configured to non-invasively applying neuromodulation of the trigeminal nerve. Non-invasive trigeminal stimulation may be applied via one or more skin surface electrodes that apply trigeminal stimulation to one or more of the subject's forehead, cheek(s), nose, tongue, or other facial skin. In some embodiments, applying the non-invasive neurostimulation to the subject's trigeminal nerve includes targeting at least one of the ophthalmic nerve, maxillary nerve, or mandibular nerve. Alternatively, in some variations, applying non-invasive neurostimulation to the subject's trigeminal nerve includes avoiding targeting at least one of the ophthalmic nerve, maxillary nerve, or mandibular nerve.

Figure 8:
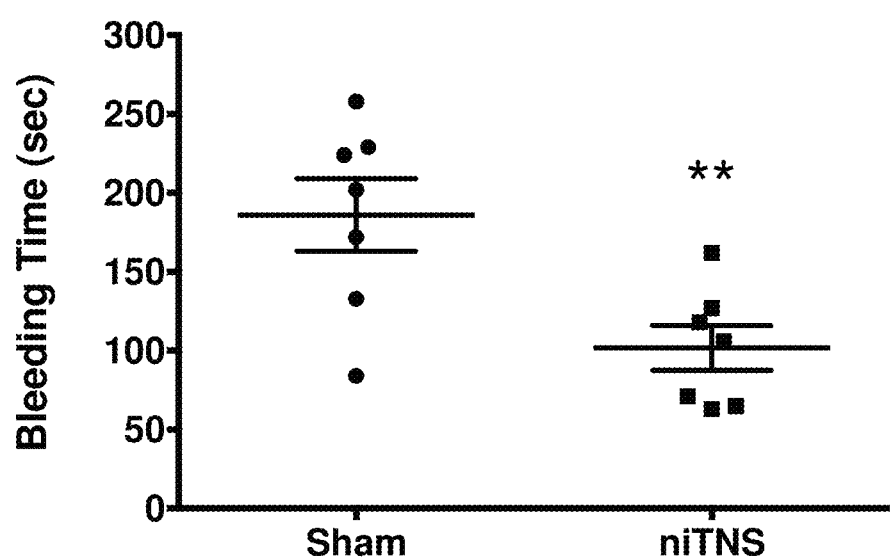
FIG. 8 is a graph showing the effect of non-invasive stimulation of the trigeminal nerve on bleeding in an animal (mouse) model.

For example, FIG. 8 illustrates the use of non-invasive stimulation in a mouse model, showing a substantial reduction in bleeding (e.g., bleed time) over control animals. In this example, noninvasive electrical stimulation of the trigeminal nerve (niTNS) was shown to reduce bleeding time in a murine model of arterial tail hemorrhage (niTNS=101.7±14.1 sec vs. Sham 186±23 sec, n=7/group, p=0.009). External electrodes applied to the animal were used to apply the electrical stimulation.

In general, any appropriate frequency and/or amplitude and/or duration may be used. In some embodiments, applying the non-invasive neurostimulation to the subject's trigeminal nerve comprises non-invasive neurostimulation has a frequency of 1-300 (e.g., between 10-60 Hz, etc.). In some embodiments, the non-invasive neurostimulation has an intensity of 2 mV-20 V (e.g., between 0.5 V and 15 V, between 1 V and 12 V, etc.). In some embodiments, the non-invasive neurostimulation has a duty cycle of between about 20% to 70% (e.g., 1 second "on" and 1-2 seconds "off"). In some embodiments, the non-invasive neurostimulation includes a pulse width of between about 0.1 ms to 10 ms (e.g., between about 0.1 ms to 5 ms, between about 0.25 to 5 ms, etc.). In some embodiments, at least one of a stimulation voltage or a current is increased gradually (e.g., steps of 0.1 V). In some embodiments, the closed-loop trigeminal nerve stimulation is conducted based on a heart rate of the animal. In some embodiments, the closed-loop trigeminal nerve stimulation is conducted based on a heart rate variability (HRV) of the animal. In some embodiments, certain parameters of the stimulation are modulated to maintain values of the parameters within a target range (e.g., preventing a hear rate or blood pressure effect, etc.).

Figure 9:
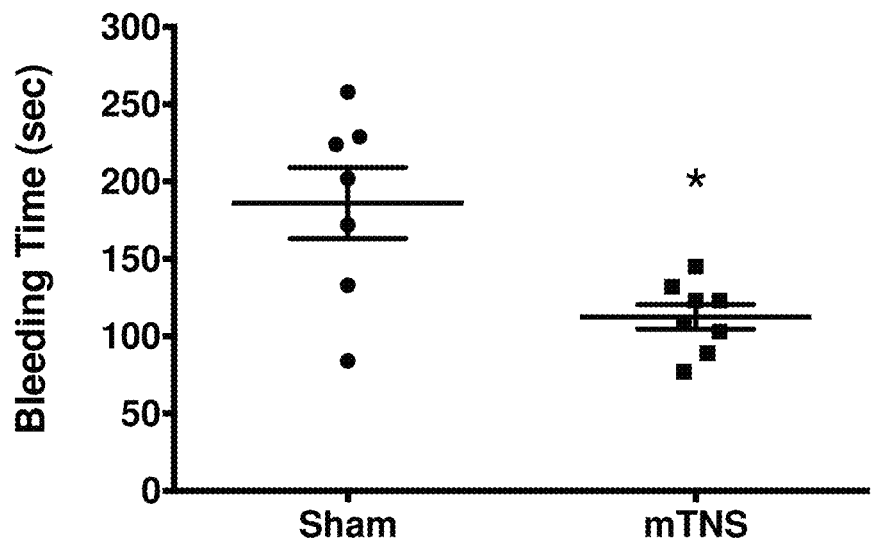
FIG. 9 is a graph showing that mechanical stimulation of the trigeminal nerve for 10 min (by pressure applied to the nerve) was sufficient to reduce bleed time in an animal (e.g., mouse) model.

Mechanical stimulation of the trigeminal nerve was also achieved by applying force to simulate the trigeminal nerve. This is illustrated in FIG. 9. In this example, mechanical stimulation of the trigeminal nerve (mTNS) reduced bleeding time in a murine model of arterial tail hemorrhage (mTNS=112.5±8 sec vs. Sham 186±23 sec, n=4-5/group, p=0.007). As mentioned above, the stimulation may be continuous (e.g., continuous mechanical pressure) and/or pulsatile (e.g., stimulation between 0.1 Hz and 500 Hz, etc.).

Figure 10:
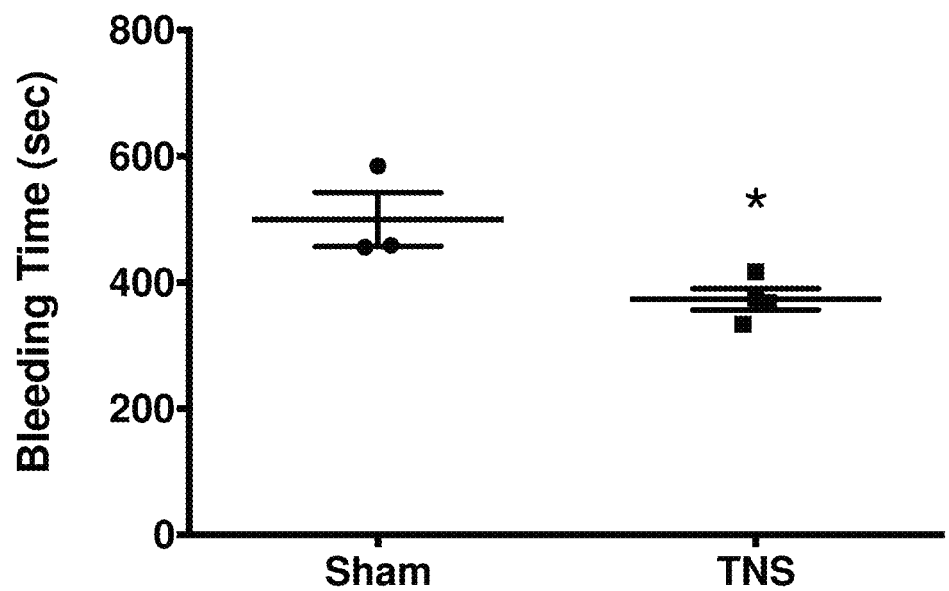
FIG. 10 is a graph showing that trigeminal nerve stimulation within the target effective range results in a significant reduction in bleeding (shown here by a reduction in bleed time) was possible even when the subject was treaded with an anti-coagulant (e.g., aspirin) prior to the trigeminal stimulation.

In general, the method and apparatuses described herein for controlling bleeding by stimulation of the trigeminal nerve may be effective even in the presence of an anticoagulant, such as aspirin. This is illustrated in FIG. 10. In this example, electrical stimulation of the trigeminal nerve (TNS) reduced bleeding time in a murine model of arterial tail hemorrhage compounded by 4 hour pretreatment with the antiplatelet agent aspirin (50 mg/kg, ip) (TNS=373.5±17.0 sec vs. Sham 500±42.5 sec, n=3-4/group, p=0.027).

The methods and apparatuses for controlling bleeding by stimulation of the trigeminal nerve described herein may be used to treat acute bleeding. For example, acute bleeding from trauma, such as from traffic and other accidents, and/or from combat, may be treated using the methods and apparatuses described herein. A patient experiencing acute bleeding may be treated by applying a patch (e.g., adhesive patch), bandage, headband, facemask, hat, helmet, etc. that includes an applicator configured to deliver trigeminal nerve stimulation in a continuous manner in order to decrease bleed time. The applicator may apply stimulation, including transdermal stimulation, to one or more regions of the trigeminal until the bleeding is controlled.

In some cases the apparatus may be integrated into work or safety equipment, including a helmet or the like, worn by a subject at risk for bleeding, including traumatic injury. For example, the subject may be part of the military, police, etc. Any of the apparatuses and methods described herein may also include one or more sensors for triggering and/or controlling the applied stimulation to the trigeminal nerve. For example, the methods and apparatuses may include sensors to detect one or more of blood pressure, pulse, etc. Thus, any of the apparatuses described herein may be configured to include one or more sensors.

Also described herein are surgical tools that may be used or useful for treating or controlling bleeding. For example, a surgical device may be configured to be attached, acutely implanted and/or inserted on or into a subject about to undergo a surgery. As described above, the methods described herein may be used ahead of a scheduled surgery (e.g., 5 minutes ahead, 10 minutes ahead, 15 minutes ahead, 20 minutes ahead, 30 minutes ahead, or more) either continuously or discretely to reduce or control bleeding during and/or after the surgery. For example, two or more tissue penetrating electrodes may be inserted into the subject's tissue at or near the trigeminal nerve so that stimulation can be applied as described above. The apparatus may be worn (as a band, e.g., headband, forehead applicator, mask, etc. and/or secured in place via a biocompatible adhesive. In some variations, these methods may be used to treat a patient following a surgery and/or following delivery of a baby (e.g., to recue bleeding due to postpartum hemorrhage or any other medical procedure in which bleeding may be a concern (e.g., spine surgery).

In addition to acute bleeding, the methods and apparatuses described herein may be used to treat chronic bleeding. For example, any of these methods and apparatuses for reducing bleeding by trigeminal stimulation may be used to treat a subject having hemophilia. As shown in the animal examples above (e.g., FIGS. 5 and 6), these methods are effective even in a dose-dependent manner for reducing bleeding in hemophilia. Hemophiliac subjects may be at risk for bleeding over their entire lives. In some cases an implant (and particular an implant that is used with an external power source/generator, such as an inductive source) may be implanted. Alternatively, a wearable (e.g., headband, hat, helmet, mask, etc.) may be used to noninvasively apply trigeminal stimulation. For example, a wearable device for applying trigeminal stimulation may be kept on hand for wearing and application when there is a risk of bleeding nearby.

Surprisingly, the methods and apparatuses described herein may be used in patients that have been given or taken a bleeding inhibitor, such as an anticoagulant, as shown in FIG. 10, above for aspirin, heparin, warfarin, rivaroxaban, dabigatran, apixaban, edoxaban, etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a hemophiliac subject, the method comprising:
    determining when the subject is bleeding; and
    applying one or more of mechanical or electrical stimulation to the subject's trigeminal nerve to reduce bleeding wherein applying said one or more of mechanical or electrical stimulation comprises avoiding triggering a diver's reflex, and thereby reducing bleeding.

2. The method of claim 1, further comprising reducing bleeding by at least 10%.

3. The method of claim 1, further comprising reducing bleeding by greater at least 20%.

4. The method of claim 1, wherein applying one or more of mechanical or electrical stimulation comprises stimulating the trigeminal nerve at between 0.1 Hz and 100 Hz for greater than 10 minutes.

5. The method of claim 1, wherein applying said one or more of mechanical or electrical stimulation comprises applying electrical stimulation noninvasively to the subject's trigeminal nerve.

6. The method of claim 1, wherein applying said one or more of mechanical or electrical stimulation comprises applying electrical stimulation between 1-50 Hz and between 0.5-15V having a pulse width of between 0.5 ms and 10 ms.

7. The method of claim 1, wherein applying said one or more of mechanical or electrical stimulation comprises applying non-invasive mechanical stimulation.

8. The method of claim 1, wherein applying said one or more of mechanical or electrical stimulation comprises stimulating one of an ophthalmic, maxillary or mandibular branch of the subject's trigeminal nerve.

9. The method of claim 1, wherein applying said one or more of mechanical or electrical stimulation comprises stimulating two or more of an ophthalmic, maxillary or mandibular branch of the subject's trigeminal nerve.

10. The method of claim 1, wherein applying said one or more of mechanical or electrical stimulation comprises stimulating sensory fibers of the subject's trigeminal nerve.

11. The method of claim 1, wherein applying said one or more of mechanical or electrical stimulation comprises applying unilateral stimulation to the subject's trigeminal nerve.

12. The method of claim 1, wherein applying said one or more of mechanical or electrical stimulation comprises applying bilateral stimulation to the subject's trigeminal nerve.

13. The method of claim 1, wherein reducing said bleeding comprises reducing said bleeding by at least 30%.

14. The method of claim 1, wherein applying said one or more of mechanical or electrical stimulation consists of stimulating the trigeminal nerve.

* * * * *